United States Patent [19]

Barberet et al.

[11] Patent Number: Plant 7,182

[45] Date of Patent: Mar. 6, 1990

[54] CARNATION NAMED LONBOLANK

[75] Inventors: Nicole Barberet; Henri Blanc, both of Antibes, France; Antonio Di Giorgio; Renato Di Giorgio, both of San Remo, Italy

[73] Assignee: Etablissements Barberet et Blanc, La Londe-les-Maures, France

[21] Appl. No.: 315,542

[22] Filed: Feb. 27, 1989

[30] Foreign Application Priority Data

Oct. 29, 1987 [ES] Spain ..... 871,195

[51] Int. Cl.[4] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new and distinct standard carnation cultivar distinguished particularly by its very large blooms of a uniform light yellow coloration, the blooms of which are striated by thin longitudinal lines of a Carmine Rose color and sometimes white which provide a very unusual character for the full flower appearance, the blooms being produced profusely at recurrent intervals from Spring to Fall on the long, strong stems of a tall plant having a vigorous, upright and rigidly strong growth habit with a moderately abundant production of foliage.

1 Drawing Sheet

BACKGROUND OF THE NEW PLANT

This new carnation variety originated as a seedling of a hybrid developed by us in 1985 at the nursery of Antonio and Renato Di Giorgio at San Remo, Italy by crossing two varieties selected from the Di Giorgio collection of carnations maintained at their nursery for breeding purposes. We selected this particular seedling for propagation because of its very large blooms having an attractive overall light yellow coloration tinged with light pink striations of its petals and being carried on long, strong, upright stems of a tall plant appearing to have excellent characteristics for commercial propagation for cut flower production. This selected seedling was propagated under our direction by means of cuttings at the Di Giorgio nursery in San Remo with such satisfactory results that we decided to continue propagation of the new plant at San Remo through several successive generations by cuttings whereby we were satisfied that the novel characteristics of the new plant would be retained from generation to generation and that its homogeneity could be assured for large-scale propagation for the production of cut flowers.

Our new carnation is now being propagated for commercial purposes by means of cuttings, as well as by in vitro propagation procedures at Establissements Barberet et Blanc, Laboratoire de Physiologie Vegetale, 83250 La Londe-Les Maures, France.

DESCRIPTION OF THE DRAWING

Our new carnation cultivar is illustrated by the accompanying photographic drawing which shows several blooming stems with flowers and buds in various stages of development, the color rendition being as nearly true to that herein specified as is reasonably possible to obtain by professional photographic procedures.

DESCRIPTION OF THE NEW PLANT

The following is a detailed description of our new variety of carnation based upon observations made in the Spring of 1988 of plants grown in greenhouse, as well as outside, at San Remo, Italy, the color designations stated herein being according to The R.H.S. Colour Chart published by the Royal Horticultural Society of London, England.

THE PLANT

Origin: Seedling.

Parentage:

*Seed parent.*—Variety No. 60.

*Pollen parent.*—Variety No. 647.

Both parents being identified in the Di Giorgio breeding records maintained at their nursery office at Via Villetta 41, 18038 San Remo, Italy.

Classification:

*Botanic.*—*Dianthus caryophyllus.*

*Commercial.*—Standard Carnation.

Form: A tall, erect bush having at least four stems emitted near the ground.

Growth rate: Quite rapid.

Main stem length: Less than 15 cm. due to pinching to encourage branching.

Branching: This plant is well branched.

Growth: Upright, vigorous and rigid.

Foliage:

*Quantity.*—Moderately abundant.

*Number of leaves.*—More than 120.

*Leaf size.*—(At the seventh node) About 12.5 cm. long and 0.8 cm. wide.

*Leaf shape.*—Linear — With acuminate tip and entire upwardly curved margins.

*Texture.*—Leathery.

*Color.*—Both upper and under sides, 189-A/B.

THE BUD

Size: Large.

*Diameter.*—Averages about 2.5 cm.

*Length.*—Averages about 3.3 cm.

Shape: Globular before sepals divide.

Rate of opening: Normal.

Color of petals: When sepals first divide, and petals begin to unfurl, the same as at full bloom.

Sepals:

*Number.*—Six or seven.

*Shape.*—Generally elliptical, with obtuse to acuminate apex.

*Character.*—The sepals are hooded over the bud before parting and stand up as the flower opens.

*Color.*—Inside, 145-D. Outside, 147-C and 145-A.

*Striae.*—Longitudinal.

Calyx:

*Shape.*—Bell-shaped.

*Size.*—Large.

*Aspect.*—Smooth.

*Splitting.*—Sometimes a little splitting occurs.

Flower Stem:

*Length.*—Averages about 74.3 cm., when cut at the tenth node.

*Character.*—Erect and moderately rigid.

*Color.*—189-A/B.

THE FLOWER

Blooming habit: Recurrent, blooming profusely in the Spring, Midseason and Fall blooming periods with a tendency to give few blooms in the Fall.

Size of flower: Very large.

*Diameter.*—Averages about 8.7 cm.

*Depth.*—Averages about 5.5 cm.

Borne: Singly on a long, strong, upright stem.

Shape: When bloom first opens, high-centered. When bloom matures, dome-shaped.

Petalage:

*Number of petals.*—Averages about ninety-six.

Arrangement.—Imbricated.

*Form.*—Fan-shaped with serrated edges.

*Texture.*—Leathery.

*Appearance.*—Satiny.

*Color.*—Both inner and outer petals: Body — 3-D, with striae of Carmine Rose, 52-C/D, and white, 155-D. Base — Greenish. Reverse side — the same as the upper side.

Petaloids:

*Number.*—Less than ten.

*Size.*—Smaller than the petals.

*Color.*—The same as the petals.

Flower stem:

*Character.*—Upright with good strength and outwardly curved foliage.

Discoloration after full bloom: Very little.

Persistence: The flower petals hang on and dry.

Fragrance: Perceptible.

Lasting quality: As a cut flower, at least ten days in vase keeping.

REPRODUCTIVE ORGANS

Stamens:

*Number.*—Varies from two to nineteen.

*Arrangement.*—Around the ovary.

*Anthers.*—Size: Less than 4 mm. Color: Yellowish.

*Filaments.*—Length: Average about 2 cm. Color: Yellowish.

Pistils:

*Number.*—Three or four.

*Styles.*—Length: About 2 cm. Color: Yellowish.

*Stigma.*—Color: Yellowish.

Character of ovaries: Ribbed.

This variety most nearly resembles the variety Londorga (U.S. Plant Pat. No. 5,784). This new carnation cultivar differs from Londorga, however, by having more striae in the flower petals and a more important number of petals.

We claim:

1. The new and distinct standard carnation variety, substantially as herein shown and described, particularly characterized by its flowers of very large size and overall light yellow coloration, the petals of which have light pink longitudinal striation, the flowers being borne singly on long, strong, upright stems of a very tall plant.

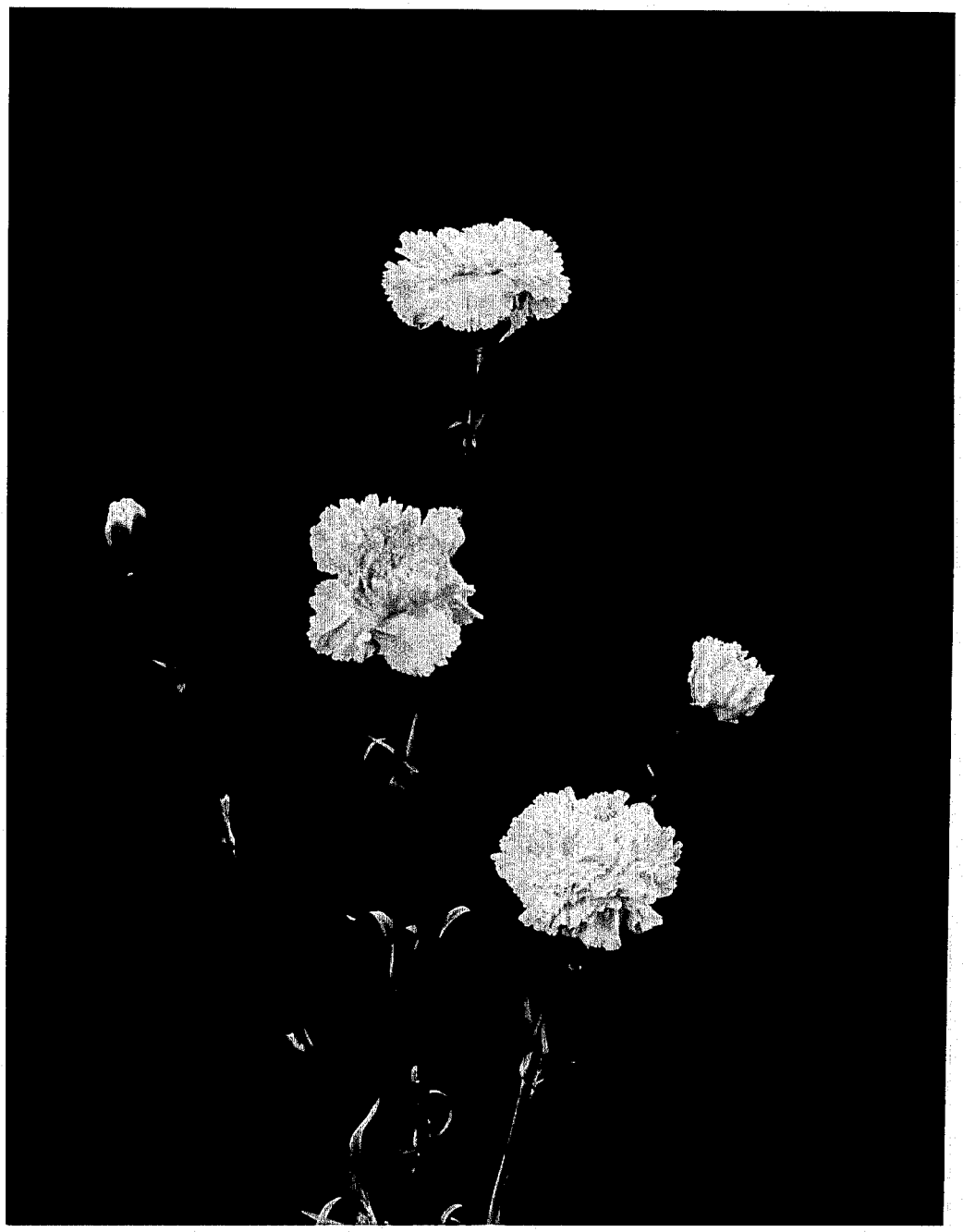

* * * * *